(12) United States Patent
Bertram, III

(10) Patent No.: US 7,942,880 B2
(45) Date of Patent: May 17, 2011

(54) GEOMETRIC REPLACEMENTS FOR DEFECTIVE BONE

(76) Inventor: Morton Bertram, III, Naples, FL (US)

( * ) Notice: Subject to any disclaimer, the term of this patent is extended or adjusted under 35 U.S.C. 154(b) by 9 days.

(21) Appl. No.: 11/061,670

(22) Filed: Feb. 18, 2005

(65) Prior Publication Data

US 2005/0182493 A1 Aug. 18, 2005

Related U.S. Application Data

(60) Provisional application No. 60/546,081, filed on Feb. 18, 2004.

(51) Int. Cl.
*A61F 5/00* (2006.01)
*A61F 2/32* (2006.01)

(52) U.S. Cl. .............. 606/86 R; 623/22.38; 623/22.36

(58) Field of Classification Search ............... 606/86 R, 606/87, 88, 89, 280, 281, 286; 623/16.11, 623/17.11, 17.17, 18.11, 19.11, 20.11, 20.14, 623/21.11, 22.21, 22.23, 22.36, 22.38, 23.31, 623/23.35; 433/201.1
See application file for complete search history.

(56) References Cited

U.S. PATENT DOCUMENTS

| | | | | |
|---|---|---|---|---|
| 3,412,733 A | * | 11/1968 | Ross ................................ 606/81 |
| 3,608,096 A | * | 9/1971 | Link ............................ 623/22.39 |
| 3,871,031 A | * | 3/1975 | Boutin ......................... 623/22.23 |
| 4,660,891 A | * | 4/1987 | Kramer-Wasserka ......... 299/81.2 |
| 4,666,449 A | * | 5/1987 | Frey et al. ................... 623/22.24 |
| 4,762,122 A | * | 8/1988 | Slocum ............................ 606/70 |
| 4,883,491 A | * | 11/1989 | Mallory et al. ............. 623/22.31 |
| 5,176,711 A | * | 1/1993 | Grimes ....................... 623/22.22 |
| 5,306,311 A | * | 4/1994 | Stone et al. ................. 623/14.12 |
| 5,361,452 A | * | 11/1994 | Horn ................................ 15/406 |
| 5,405,389 A | * | 4/1995 | Conta et al. ................. 623/23.55 |
| 5,549,692 A | * | 8/1996 | Hauser et al. ................. 623/22.3 |
| 5,904,684 A | * | 5/1999 | Rooks .............................. 606/69 |
| 6,162,257 A | * | 12/2000 | Gustilo et al. .............. 623/22.32 |
| 6,200,347 B1 | * | 3/2001 | Anderson et al. ........... 623/16.11 |
| 6,855,167 B2 | * | 2/2005 | Shimp et al. ................ 623/17.11 |
| 6,902,578 B1 | * | 6/2005 | Anderson et al. ........... 623/16.11 |

* cited by examiner

*Primary Examiner* — David Isabella
*Assistant Examiner* — Joshua Levine
(74) *Attorney, Agent, or Firm* — Gifford, Krass, Sprinkle, Anderson & Citkowski, P.C.

(57) ABSTRACT

In the repair of bone voids and deficiencies, rather than forming a planar, angled surface that could result in a "slip plane," an implant features a defined geometric pattern such as a stair-step, which mates with a corresponding stair-step pattern formed on the bone. Screws or alternative fasteners extend through one or more of the stair-step patterns, and into the bone, such that local interface around each fastener is substantially transverse to the axis of the fastener, thereby achieving a set of effective, compression bond. As such, shear stresses that might be associated with an angled, planar fixation are converted to compressive forces, leading to a longer life and a reduced need for revision. Although in the preferred embodiment the plurality of surfaces defines a stair-step having right angles, other geometric patterns are applicable, so long as an irregular defect may be made more regular, and/or compressive forces are used to prevent shear stress. Cementation for may be used for fixation, and/or bone in-growth/on-growth. Although the invention is described in terms of the repair of a deficient acetabulum, the general idea is applicable to any region of the bone including, without limitation, glenoid repair, and tibial repair.

4 Claims, 3 Drawing Sheets

US 7,942,880 B2

GEOMETRIC REPLACEMENTS FOR DEFECTIVE BONE

REFERENCE TO RELATED APPLICATION

This application claims priority from U.S. Provisional Patent Application Ser. No. 60/546,081, filed Feb. 18, 2004, the entire content of which is incorporated herein by reference.

FIELD OF THE INVENTION

This invention relates generally to the repair of bone loss and, in particular, to the use of an implant having a geometric bone-contacting surface operative to promote compression bonding and minimize premature failure caused by 'slip planes.'

BACKGROUND OF THE INVENTION

With respect to the hip, FIG. 1 shows a prior-art situation, wherein a portion 110 of a socket associated with the pelvis 102 is deficient or otherwise defective, such that interaction with the head 104 of a proximal femur is inadequate and/or painful. Currently, although the portion 110 may be replaced, it is done on a generally hand-crafted basis. Typically, a planar, angled surface is formed in the acetabulum, and an implant having a corresponding planar surface is affixed thereto. The problem is that forces created in the hip may apply shear stresses to the implant, leading to premature failure.

SUMMARY OF THE INVENTION

This invention is directed to the repair of bone voids and deficiencies, but instead of forming a planar, angled surface that could result in a "slip plane," the invention utilizes an implant having a defined geometric pattern such as a stair-step, which mates with a corresponding stair-step pattern formed on the bone. Screws or alternative fasteners extend through one or more of the stair-step patterns, and into the bone, such that local interface around each fastener is substantially transverse to the axis of the fastener, thereby achieving a set of effective, compression bond. As such, shear stresses that might be associated with an angled, planar fixation are converted to compressive forces, leading to a longer life and a reduced need for revision.

An implant according to the invention includes a body having a bone-contacting side with a plurality of surfaces, each on a different plane, and at least one aperture extending through the body and one of the surfaces, the aperture defining an axis substantially transverse to the surface where it extends therethrough. Although in the preferred embodiment the plurality of surfaces defines a stair-step having right angles, other geometric patterns are applicable, so long as an irregular defect may be made more regular, and/or compressive forces are used to prevent shear stress. For example, sawtooth, wavy or undulating, and combinations thereof, may alternatively be used. Cementation for may be used for fixation, and/or bone in-growth/on-growth. Furthermore, although the invention is described in terms of the repair of a deficient acetabulum, it will be appreciated that the general idea is applicable to any region of the bone including, without limitation, glenoid repair, tibial repair, and so forth.

DETAILED DESCRIPTION OF THE INVENTION

Figure 1:
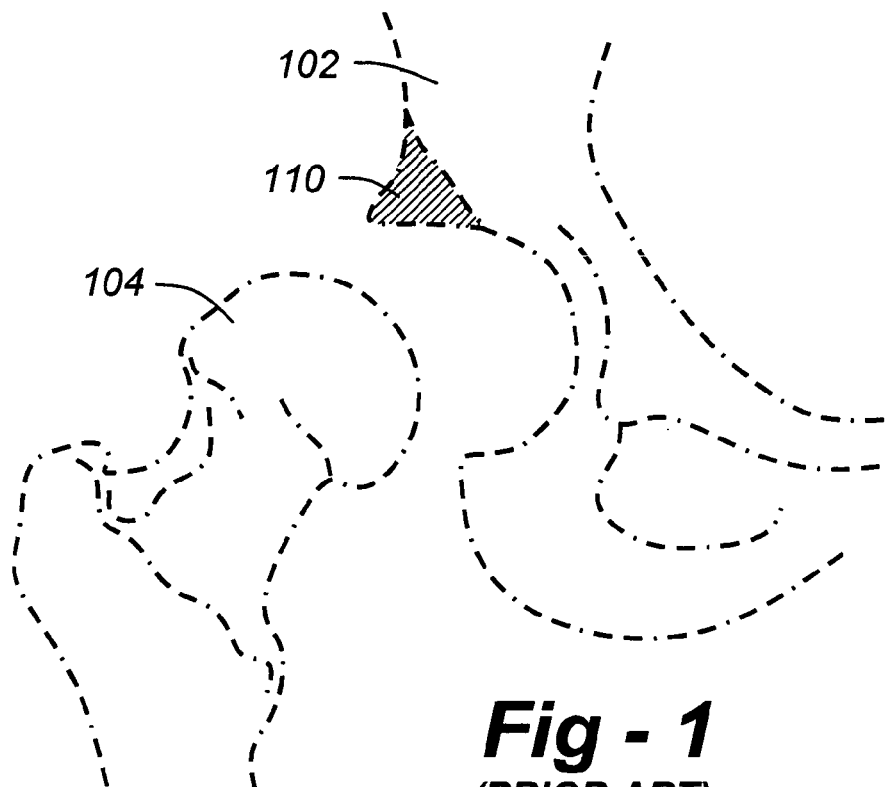
FIG. 1 is a drawing of a prior art hip replacement system.
Figure 2:
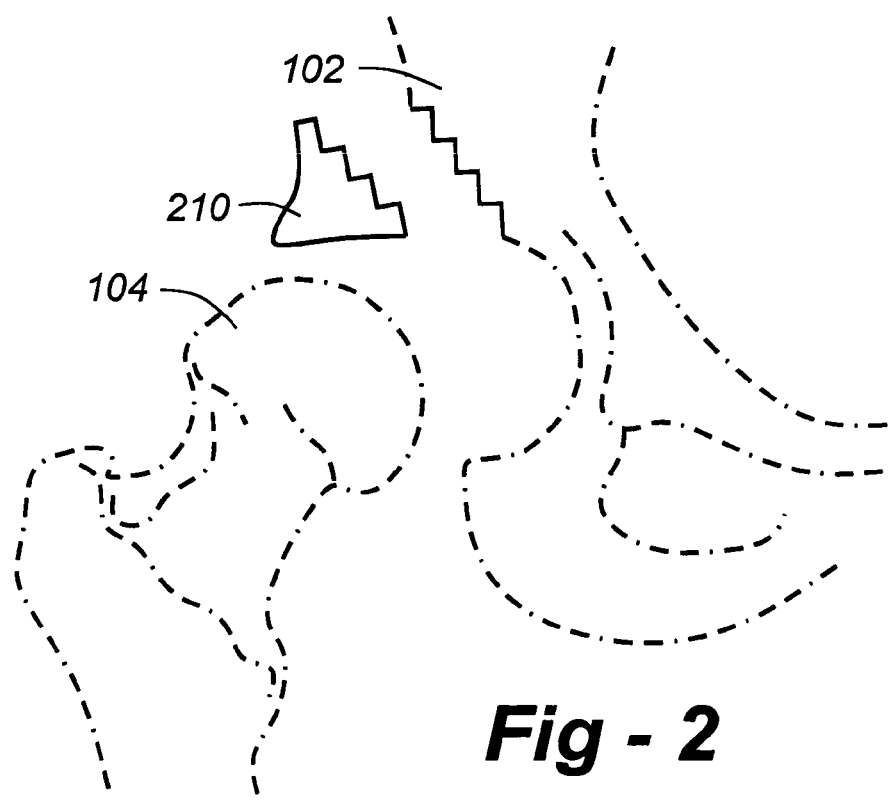
FIG. 2 is a drawing which shows a broad application of the invention, namely, the use of an implant having a defined geometric pattern such as a stairstep.

FIG. 2 is a drawing which shows a broad application of the invention. A bone such as pelvis 102 includes a defective region, but instead of forming a planar, angled surface that could result in a "slip plane," the invention utilizes an implant 210 having a defined geometric pattern such as a stairstep, which mates with a corresponding stairstep pattern on the pelvis 102.

Figure 3:
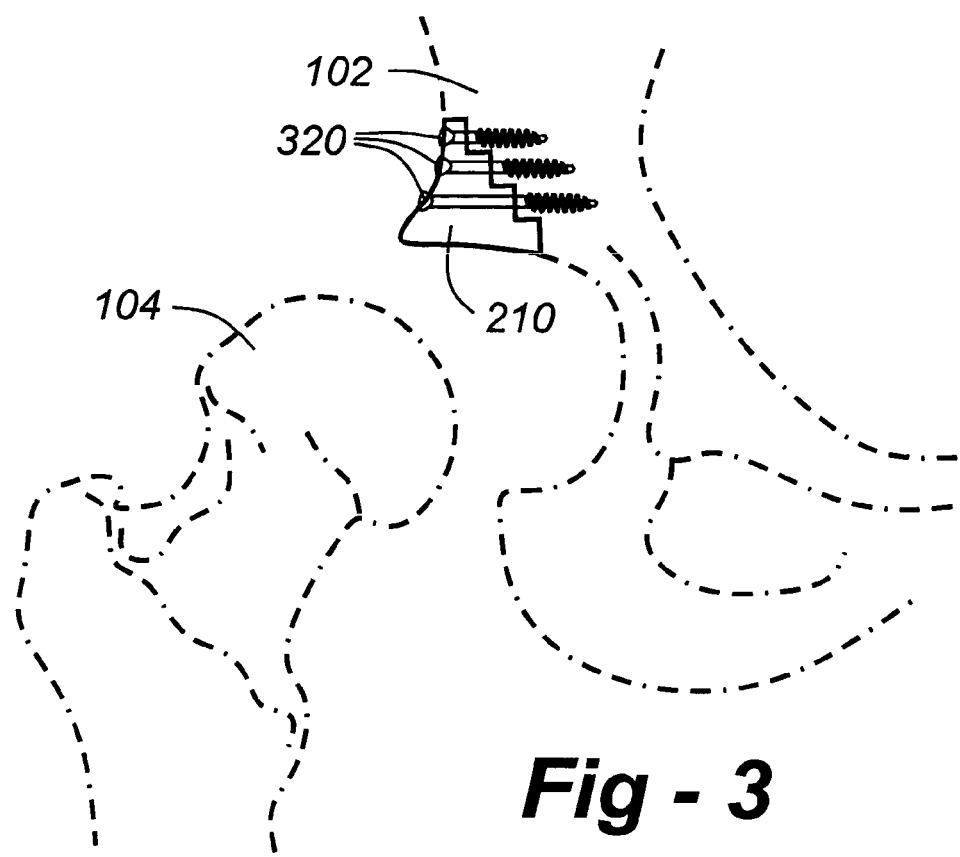
FIG. 3 shows how an inventive component would preferably be attached, namely, utilizing supplemental screws.

FIG. 3 shows how the component 210 would preferably be attached, namely, utilizing supplemental screws 320 which extend through one or more of the stairstep patterns, and into the bone, such that local interface around each fastener is substantially transverse to the axis of the fastener, thereby achieving a set of effective, compression bond. As such, shear stresses that might be associated with an angled, planar fixation are converted to compressive forces, leading to a longer life and a reduced need for revision.

Figure 4:
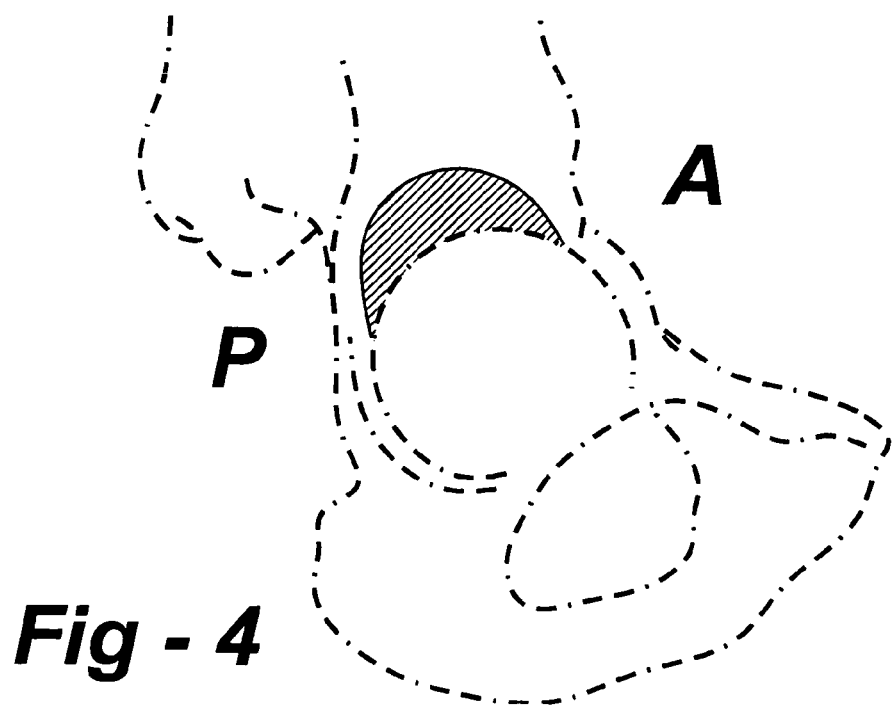
FIG. 4 is a lateral view showing the defective region oriented along anterior (A) and posterior (P) directions.
Figure 5:
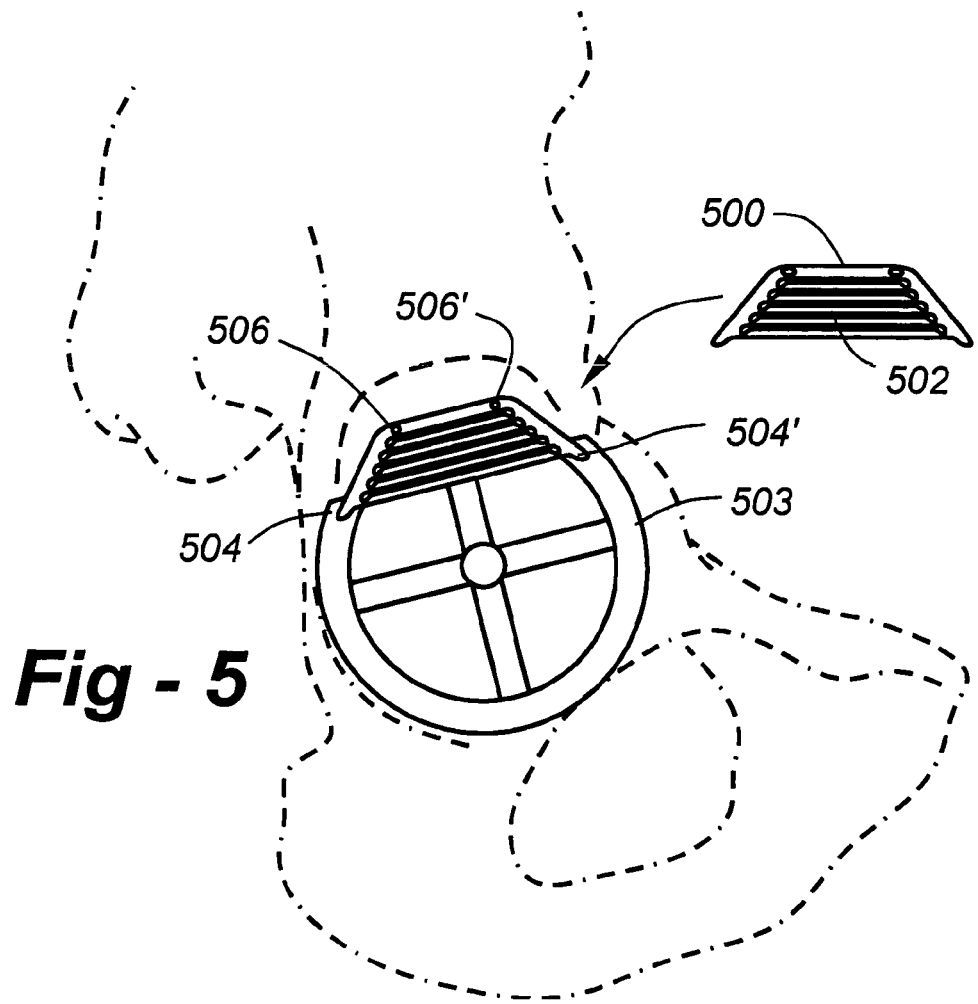
FIG. 5 illustrates the use of a guide according to the invention having slots into which some sort of cutting device may be journaled to produce the geometric pattern in the bone.

FIG. 4 is a lateral view showing a defective region (hatched) oriented along anterior (A) and posterior (P) directions. FIG. 5 illustrates the use of a guide 500 according to the invention, having slots 502 into which a cutting device may be journaled to produce the geometric pattern in the bone. The guide 500 may take advantage of a shell 503 in the form of an acetabular trial cup which consumes less than a hemisphere, and which terminates with points 504 and 504' to which the guide 500 may be attached.

Figure 6:
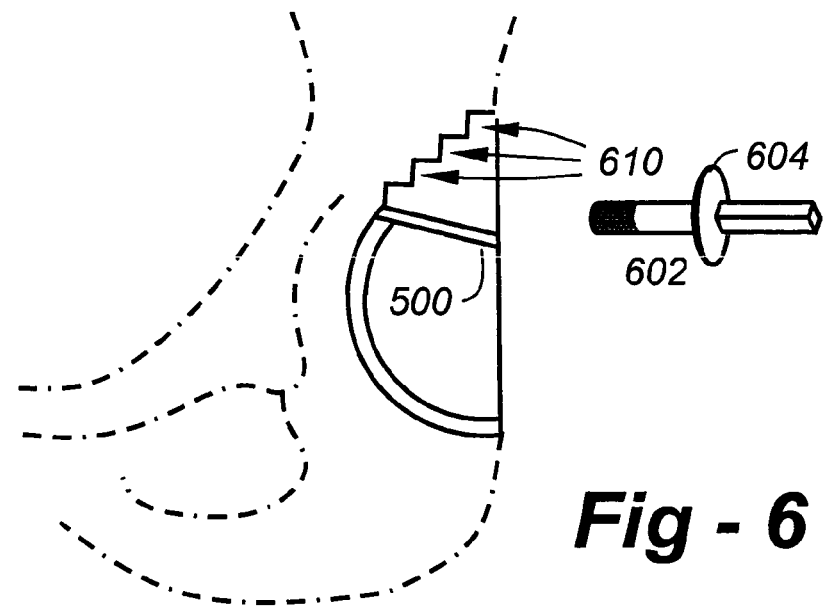
FIG. 6 is a drawing of a burr to be used in a guide to produce a stairstep pattern.

Pins 506, 506' may be used to hold the guide in place for further stability relative to the defective region, allowing a burr such as 602 shown in FIG. 6 to be used in the guide 500 to cut the stairstep pattern 610. The burr may be an existing design, such as that provided by the Stryker Corporation under its "TPS" system, which includes a round collar that prevents it from sinking below the level of the channel or groove into which it fits. Alternatively, a special burr may be designed for the purposes set forth herein.

It will further be noted that, although in the preferred embodiment, the geometric pattern formed in the bone is a stairstep having right angles, other geometric patterns are applicable, so long as an irregular defect may be made more regular, and/or compressive forces are used to prevent shear stress. For example, sawtooth, wavy or undulating, and combinations thereof, may alternatively be used. Cementation for may be used for fixation, and/or bone in-growth/on-growth.

I claim:
1. A method of repairing a defective region in a bone, comprising the steps of:
   providing a body having a bone-contacting side with a plurality of surfaces, each on different parallel planes, and at least one aperture extending through the body and one of the surfaces, the aperture defining an axis substantially transverse to the surface where it extends therethrough;
forming a pattern in a bone, the pattern including a plurality of spaced-apart surfaces on different parallel planes corresponding to the surfaces of the implant;
positioning the implant such that the surfaces of the implant and the bone are in alignment; and
installing a fastener through the aperture and into the bone such that the implant is at least locally held in position using compression.

2. The method of claim 1, wherein the pattern is a stair-step pattern.

3. The method of claim 1, wherein the spaced-apart surfaces are parallel to one another.

4. The method of claim 1, wherein the bone includes a portion of an acetabular rim.

* * * * *